United States Patent [19]

Thoene

[11] Patent Number: 5,554,655
[45] Date of Patent: Sep. 10, 1996

[54] METHOD OF TREATING HIV INFECTION

[75] Inventor: Jess G. Thoene, 1308 Brooks, Ann Arbor, Mich. 48103

[73] Assignee: Jess G. Thoene, Ann Arbor, Mich.

[21] Appl. No.: 229,142

[22] Filed: Apr. 15, 1994

Related U.S. Application Data

[63] Continuation of Ser. No. 017,994, Feb. 16, 1993, abandoned, which is a continuation of Ser. No. 767,802, Sep. 30, 1991, abandoned.

[51] Int. Cl.$^6$ ................................................. A61K 31/13
[52] U.S. Cl. ............................................ 514/665; 514/114
[58] Field of Search ................................... 514/114, 665

[56] References Cited

U.S. PATENT DOCUMENTS

| | | | |
|---|---|---|---|
| 3,892,824 | 7/1975 | Piper et al. | 260/944 |
| 3,991,190 | 11/1976 | Garzia et al. | 260/944 |

FOREIGN PATENT DOCUMENTS

| | | | |
|---|---|---|---|
| 1157774 | 11/1983 | Canada | 31/255 |
| 0174912 | 9/1985 | European Pat. Off. | A61K 31/66 |
| 0204989 | 12/1986 | European Pat. Off. | |
| WO-A-9008540 | 8/1990 | WIPO. | |
| WO-A-9014007 | 11/1990 | WIPO. | |
| WO-A-9404185 | 3/1994 | WIPO. | |

OTHER PUBLICATIONS

Merck Index 10th ed. #2771 & 2773.
Oxford 78CA: 119655t 1973.
Hotz 81CA: 101420q 1974.
Schroeder et al. 110CA: 18156e 1989.
Pisoni et al, *J. Bio. Chem.*, vol. 260, No. 8, pp. 4791–4798, (1985).
Thoene et al, *J. of Ped.*, vol. 96, No. 6, pp. 1043–1044, (1980).
Thoene et al, *J. Clin. Invest.*, vol. 58, pp. 180–189, (1976).
Ca 78: 119655t 1973.
CA 85:28782k 1976.
CA 113: 55076m 1990.
CA 112: 48337y 1990.
CA 117: 258256a 1992.
Windholtz, "The Merck Index", 10th edition, published 1983 by Merck & Co., Inc. items 2773, 2775 and 2776 1983.
CA 107: 108862z 1987.
CA 84: 155677j 1976.
CA 75: 85659t 1971 1971.
Ryser et al, *Proc. Natl. Acad. Sci. USA*, vol. 91, pp. 4559–4563 (1994).
Bergamini et al, *J. Clin. Invest.*, vol. 93, pp. 2251–2257 (1994).
*The Journal of Clinical Investigation*, (1994), 93, pp. 2251–2257, "Cystamine Potently Suppresses in Vitro HIV Replication in Acutely and Chronically Infected human Cells", A. Bergamini et al.

*Clinically Research*, (1992), 40, p. 264A, "In–Vitro Effectiveness of Aminothiols And Disulfides Against HIV-1'", J. Thoene.
*NATO ASI SER.*, (1986), 120, pp. 329–342, "Inhibition Of HTLV–III Replication In Cell Cultures", P.S. Sarin et al.
*Proc. Natl. Acad. Sci.*, (1991), 88, pp. 986–990, "Suppression of Human Immunodeficiency Virus Expression in Chronicallly Infected Monocytic Cells By Glutathione, Glutathione Ester, And N–Acetylcysteine", Kalebic et al.
*Carinogenesis*, (1991), 12, pp. 241–247, "Modulation of Glutathoine Content and the effect on Methionine Auxotrophy and Cellular Distribution of Homocysteine and Cysteine in Mouse Cell Lines", Djurhuus et al.
*Arzneimittel Forschung*, (1986), 36, pp. 1531–1534, "Treatment of HTLV–III /LAV–Infected Patients with D–Penicillamine", R. Schulof et al.
*Aids Research And Human Retroviruses*, (1990), 6, pp.919–927, "2,3 Dimercapto–1–Propanol Inhibits HIV–1 tat Activity, Viral Production, and Infectivity In Vitro", S. Kubota et al.
*Fields Virology*, 2nd Ed., B. N. Fields, et al. Eds., Raven Press, NY, vol. 1, pp. 1075–1089 (1990).
*Fields Virology*, 2nd Ed. B. N. Fields, et al. Eds. Raven Press, NY, vol. 2, pp. 1437–1440, 1452–1477, (1990).
*Fields Virology*, 2nd Ed. B. N. Fields, et al. Eds. Raven Press, NY, vol. 1, pp. 507–548 (1990).
*Fields Virology*, 2nd Ed. B. N. Fields, et al. Eds., Raven Press, NY, vol. 2, pp. 1787–1790 (1990).
*Fields Virology*, 2nd Ed. B. N. Fields, et al. Eds. Raven Press, NY, vol. 2, pp. 1529–1543, (1990).
Dagani, *C&EN*, Nov. 23, 1987, pp. 41–49.
Droge et al, *Am. J. Med.*, vol. 91, pp. 140S–144S, (1991).
Mihm et al, *AIDS*, vol. 5, pp. 497–503 (1991).
Perrin et al, *Pharmac. Ther.*, vol. 12, pp. 255–297 (1981).
Pompei et al, *Experientia*, vol. 33, pp. 1151–1152 (1977).
La Colla et al, *Ann. NY Acad. Sci.* vol. 284, pp. 294–304 (1977).
La Colla et al, *Experientia*, vol. 31, pp. 797–798, (1975).
Marcialis et al, *Experientia*, vol. 29, pp. 1559–1661 (1973).
Schivo et al, *Experientia*, vol. 32, pp. 911–913 (1976).
*Billard et al, Antimicrobial Agents and Chemotherapy*, vol. 5, pp. 19–24 (1974).
M. S. Marcialis et al, *Experientia*, vol. 30, pp. 1272–1273 (1974).
Staal et al, *The Lancet*, vol. 339, pp. 909–912 (1992).
Roederer et al, *Proc. Natl. Acad. Sci. USA*, vol. 87, pp. 4884–4888, (1990).
Oxford et al, *J. Gen. Virol.*, vol. 18, pp. 11–19 (1973).
Oxford et al, *Ann. NY Acad.*, vol. 284, pp. 613–623 (1977).
Arora et al, *Can. J. Biochem.*, vol. 58, pp. 67–72 919800.
Gliniak et al, *J. Bio. Chem.*, vol. 266, No. 34, pp. 22991–22997, (1991).

(List continued on next page.)

Primary Examiner—Russell Travers
Attorney, Agent, or Firm—Oblon, Spivak, McClelland, Maier & Neustadt, P.C.

[57] ABSTRACT

Cysteamine, cystamine, and phosphocysteamine are effective agents for the treatment of HIV infections.

18 Claims, No Drawings

OTHER PUBLICATIONS

Leonard et al, *J. Bio. Chem.*, vol. 265, No. 18, pp. 10373–10382, (1990).

Lekutis et al, *J. Acq. Imm. Def. Syn.*, vol. 5, pp. 78–81, (1992).

Papadopolus–Eleopulos et al, *The Lancet*, vol. 338, pp. 1013–1014, (1991).

Cardin et al, *J. Biol. Chem.*, vol. 266, No. 20, pp. 13355–13363, (1991). (Abstract).

Kim et al, *Biochem. Biophys. Res. Comm.*, vol. 179, No. 3, pp. 1614–1619, (1991).

Gahl et al, *New Engl. J. Med.*, vol. 316, pp. 971–977, (1987).

Wilson et al, *J. Am. Chem. Soc.*, vol. 102, pp. 359–363, (1980).

Smolin et al, *Ped. Res.*, vol. 23, No. 6, pp. 616–620, (1988).

Owens et al, *Virology*, vol. 179, pp. 827–833, (1990).

Willey et al, *Proc. Natl. Aca. Sci. USA*, vol. 85, pp. 9580–9584, (1988).

Dedera et al, *J. Vir.*, vol. 65, No. 11, pp. 6129–6136, (1991).

Harakeh et al, *Am. Clin. Nutr.*, vol. 54, pp. 1231S–1235S, (1991).

Bacq, *Chemical Protection Against Ionizing Radiation*, IV, "The Protective Compounds", pp. 16–35., Charles C. Thomas, USA.

Thoene, "Orphan Drugs and Orphan Diseases: Clinical Realities and Public Policy," pp. 125–131, Alan R. Liss, Inc., NY, 1983.

Thoene, "Cooperative Approaches to Res. and Dev. of Orphan Drugs", pp. 157–162, Alan R. Liss, Inc., 1985.

Turner, *Med. J. Austral.*, vol. 153, pp. 502, (1990).

METHOD OF TREATING HIV INFECTION

This application is a Continuation of application Ser. No. 08/017,994, filed on Feb. 16, 1993, which was a Continuation of application Ser. No. 07/767,802, filed on Sep. 30, 1991, both now abandoned.

BACKGROUND OF THE INVENTION

1. Field of the Invention

The present invention relates to a method of treating HIV infections, and diseases caused by such infections, such as AIDS, ARC and related expressions of human immunodeficiency virus (HIV), such as lymphadenopathy, by administering cysteamine, cystamine, phosphocysteamine, or a pharmaceutically acceptable salt thereof to a patient suffering from HIV infection.

2. Discussion of the Background

Acquired immunodeficiency syndrome (AIDS) and AIDS related complex (ARC) result from infection with human immunodeficiency virus (HIV). The need for an effective treatment of AIDS, ARC and lymphadenopathy is great, due to the continuing increase of HIV infections and consequent opportunistic infections in the population. Current epidemiologic data show that infection with HIV leads to AIDS in over 90% of affected individuals within a ten-year period. The number of individuals already infected means that the number of AIDS cases will continue to increase for the foreseeable future.

AZT (zidovudine) has been recommended for the treatment of AIDS and ARC. However, results are less than satisfactory. In particular, AZT therapy is known to cause severe side effects, such as anemia. In addition, there are strains of HIV-1 which are resistant to treatment with AZT.

Penicillamine has also been recommended for the treatment of HIV infections (Schulof et al, *Arzneimittal Forschung*, vol. 36 (10), pp. 1531–1534 (1986)). However, this treatment is complicated by the toxicity of penicillamine.

Thus, there remains a need for an effective treatment of HIV infection and AIDS, ARC, and lymphadenopathy.

SUMMARY OF THE INVENTION

Accordingly, one object of the present invention is to provide a novel method for the treatment of HIV infections.

It is another object of the present invention to provide a method of treating AIDS.

It is another object of the present invention to provide a novel method for treating ARC.

It is another object of the present invention to provide a novel method for treating lymphadenopathy.

These and other objects, which will become apparent during the following detailed description have been achieved by the inventors' discovery that HIV infections and diseases, such as AIDS, ARC and lymphadenopathy may be treated by administering an effective amount of cysteamine, cystamine, phosphocysteamine, a pharmaceutically acceptable salt thereof, or a prodrug thereof, to a patient in need thereof.

DETAILED DESCRIPTION OF THE PREFERRED EMBODIMENTS

Cysteamine is a known compound of the formula $HSCH_2CH_2NH_2$.

Cysteamine may be prepared from ethanolamine and carbon disulfide via 2-mercaptothiazoline as described in Gabriel et al, *Ber.*, vol. 31, 2837 (1898); Knorr et al, *Ber.*, vol. 36, 1281 (1903); and Mills et al, *J. Am. Chem. Soc.*, vol. 62, 1173 (1940); or via ethyleneimine as described in Wenker, *J. Am. Chem. Soc.*, vol. 57, 2328 (1935); Mills et al, *J. Am. Chem. Soc.*, vol. 62, 1173 (1940); and Shirley, *Preparation of Organic Intermediates*, Wiley, NY, p. 189 (1951).

Cysteamine is useful for the treatment of nephropathic cystinosis: Thoene et al, *The Journal of Clinical Investigation*, vol. 58, pp. 180–189 (1976); Thoene et al, *The Journal of Pediatrics*, vol. 96, pp 1043–1044 (1980); Thoene, in *Orphan Drugs and Orphan Diseases: Clinical Realities and Public Policy*, Alan R. Liss, NY, pp 125–131 (1983); Thoene, in *Cooperative Approaches to Research and Development of Orphan Drugs*, Alan R. Liss, NY, pp. 157–162 (1985); Pisoni et al, *The Journal of Biological Chemistry*, vol. 260, pp. 4791–4798 (1985); Gahl et al, *New England Journal of Medicine*, vol. 316, pp. 971–977 (1987); and Smolin et al, *Pediatric Research*, vol. 23, pp. 616–620 (1988). Cysteamine is known to be safe for use in humans and does not give rise to any serious known side-effects.

Cystamine is also a known compound of the formula $(H_2NCH_2CH_2)_2S_2$.

Cystamine may be prepared by the $H_2O_2$ oxidation of cysteamine: Mills, Jr. et al, *J. Am. Chem. Soc.*, vol. 62, 1173 (1940) and Barnett, *J. Chem. Soc.*, 1944, 5.

Phosphocysteamine is the phosphorothioester of cysteamine and has the formula $$HO-\underset{\underset{OH}{|}}{\overset{\overset{O}{\|}}{P}}-S-CH_2CH_2NH_2.$$

Phosphocysteamine is also known to be useful for the treatment of nephropathic cystinosis: Thoene et al, *The Journal of Pediatrics*, vol. 96, pp. 1043–1044 (1980); Thoene, in *Cooperative Approaches to Research and Development of Orphan Drugs*, Alan R. Liss, NY, pp. 157–162 (1985); and Smolin et al, *Pediatric Research*, vol. 23, pp. 616–620 (1988).

Thus, the present invention relates to a method of treating HIV infections and diseases, such as AIDS, ARC and lymphadenopathy, said method comprising or consisting of administering an effective amount of cysteamine, cystamine, phosphocysteamine, or a pharmaceutically acceptable salt thereof to a patient in need thereof.

Although the exact dosage of cysteamine or a pharmaceutically acceptable salt thereof to be administered will vary according to the size and condition of the patient, a suitable daily dosage range for children is 1 to 3 g/m² of body surface of free base in four divided doses, preferably 1.5 to 2.5 g/m² of body surface in four divided doses, most preferably about 1.95 g/m² of body surface, in four divided doses. For adults, a suitable daily dosage is 1 to 3 g of cysteamine free base q6°; preferably 1.5 to 2.5 g, most preferably about 2 g. In the case, of a pharmaceutically acceptable salt, the dosage should be adjusted to result in administration of the same molar amount of cysteamine by taking into account the relative molecular weights of cysteamine and the salt thereof.

In the case of cystamine, the suitable, preferred and most preferred dosages correspond to the same respective dosages of cysteamine. In the case of phosphocysteamine, the suitable, preferred and most preferred dosages are selected such that the administration of the corresponding number of moles cysteamine is achieved, by taking into account the relative molecular weights of cysteamine and phosphocysteamine.

The cysteamine, cystamine, phosphocysteamine, or pharmaceutically acceptable salt thereof may be suitably administered according to the present invention intravenously, parenterally, or orally. Oral administration is preferred. The cysteamine, cystamine, phosphocysteamine, or pharmaceutically acceptable salt thereof may be administered in any conventional form such as a pharmaceutical composition. Suitable pharmaceutical compositions are those containing, in addition to cysteamine, cystamine, phosphocysteamine, or pharmaceutically acceptable salt thereof, a pharmaceutically acceptable carrier, such as water, starch, sugar, etc. The composition may also contain flavoring agents and may take the form of a solution, tablet, pill, capsule, etc. The ratio of the weight of cysteamine, cystamine, phosphocysteamine, or pharmaceutically acceptable salt thereof to the weight of the pharmaceutical composition may, of course, vary but is suitably within 1:1 to 1:5000.

It is to be understood that the present method includes embodiments in which cysteamine, cystamine, phosphocysteamine, or pharmaceutically acceptable salt thereof is administered to a patient who is also receiving AZT, DDI or any other AIDS treatment drug. The present compound(s) and AZT or DDI may be administered to the patient in a single composition comprising both the present compounds and AZT or DDI. Alternatively, the present compound(s) and AZT or DDI may be administered separately. Further, the present method includes embodiments in which AZT or DDI is administered, without cysteamine, cystamine, phosphocysteamine, or a pharmaceutically acceptable salt thereof, for a suitable time period of hours, days, or weeks, and the AZT or DDI therapy is either preceded or followed by administration of cysteamine, cystamine, phosphocysteamine, or a pharmaceutically acceptable salt, either with or without AZT or DDI.

In another embodiment, it may be preferred to coadminister cysteine along with cysteamine, cystamine, phosphocysteamine or salt thereof, to prolong the serum half-life of the cysteamine, cystamine, phosphocysteamine or salt thereof. Of course, the present method also includes administration of mixtures of cysteamine, cystamine, phosphocysteamine or salts thereof.

For purposes of the present invention, the term pharmaceutically acceptable salt thereof refers to any salt of cysteamine, cystamine, or phosphocysteamine which is pharmaceutically acceptable and does not greatly reduce or inhibit the activity of cysteamine, cystamine, or phosphocysteamine. Suitable examples include acid addition salts, with an organic or inorganic acid such as acetate, tartrate, trifluoroacetate, lactate, maleate, fumarate, citrate, methane sulfonate, sulfate, phosphate, nitrate, or chloride. In addition, for phosphocysteamine either or both of the hydrogen atoms on the phosphoryl group may be replaced with any suitable cation, such as $Na^+$, $K^+$, $Mg^{+2}$, $Ca^{++}$, $NH_4$, or $NR_4^+$ (where R is $C_{1-4}$ alkyl).

It is to be further understood that the terms cysteamine, cystamine, phosphocysteamine, and pharmaceutically acceptable salts thereof include all the hydrated forms of these compounds as well as the anhydrous forms.

It is to be understood that the present method also encompasses the administration of prodrugs of cysteamine, cystamine, or phosphocysteamine. By prodrug is meant any compound that is metabolized to cysteamine, cystamine or phosphocysteamine by the body.

Thus, cysteamine and cystamine have now been shown to protect HIV-infected cells from the cytopathic effects of the viral infection, without exhibiting any cytotoxic effect on uninfected cells. Although not intended to be limiting in any way, a possible explanation for the efficacy of cysteamine for the treatment of HIV infections is as follows.

Human immunodeficiency virus contains two coat proteins (GP120 and GP41). GP120 is a transmembrane protein which forms a domain on the exterior surface of the virus which recognizes the CD4 receptor on a subpopulation of T lymphocytes. It is thought that the recognition between the GP120 coat protein and the CD4 receptor not only leads to infection of cells by the virus but also mediates cell death by promoting autofusion, syncytia formation, and other toxic effects not yet well characterized. Crucial to the above reaction is the presence of disulfide bonds which maintain the tertiary structure of the exterior portion of GP120. It is these intrachain disulfide bonds that may be the target for cysteamine. Cysteamine is known to be highly effective in promoting intrachain disulfide scission by direct reaction with the disulfides, leading to mixed disulfides at each end of the pre-existing cystine resides. Such a reaction may lead to disruption of the tertiary structure of the GP120 molecule, altering its configuration, and inhibit binding to the CD4 receptor, inhibiting viral entry, autofusion, and other toxic effects of HIV.

Although the present method may be utilized to treat HIV infection at any stage, it is preferred that the treatment be initiated before the onset of frank AIDS or ARC, so that the development of frank AIDS or ARC may be prevented.

Other features of the invention will become apparent in the course of the following descriptions of exemplary embodiments which are given for illustration of the invention and are not intended to be limiting thereof.

EXAMPLES

The effectiveness of cysteamine and cystamine for the treatment of HIV infection was determined as follows.

The assay of cysteamine and cystamine was performed using the CEM human T-lymphocyte cell line as host cells, and the HTLV-III$_B$ strain of HIV-1 as the challenge virus. Cells were first pretreated with the test samples, then infected at a low multiplicity with virus. Twice each day an aliquot of fresh drug was added to the cultures, and the assay was monitored microscopically for signs of virus infection. Starting six days after infection, daily cell counts were performed on the cell and virus control samples to monitor the cell growth and viability. On about the seventh or eighth day postinfection, when viral CPE was maximal as determined by the cell counts, a quantitative colorimetric assay was performed to determine the extent of antiviral activity of the test samples. This assay utilized the metabolic reduction of 3-(4,5-dimethylthiazole- 2-yl)-2,5-diphenyl-tetrazolium bromide (MTT) by cells surviving the virus challenge as an indication of the drug-induced suppression of viral CPE.

Cysteamine and cystamine were dissolved in a suitable solvent at a concentration of 100 mM (100× for the top dose), and several aliquots were frozen at −90° C. Dilutions were made in RPMI-1640 medium containing 2 mM L-glutamine and 25 mM HEPES, and supplemented with 10% fetal bovine serum, 50 units of penicillin G per ml, and 50μg streptomycin sulfate per ml. Cysteamine and cystamine were assayed at concentrations of 1 mM, 0.1 mM, and 0.01 mM.

The assay was done in 96-well tissue culture plates. A volume containing 1×10$^4$ CEM cells was dispensed into each well. Each dilution of the test compound (prepared as a 4× concentration) was added to six wells of cells, and the cells were incubated at 37° C. for one hour. 1000 TCID$_{50}$ of a frozen culture of HIV-1 was added to four of the wells for each test compound concentration. This resulted in a multiplicity of infection of 0.1 for the HIV-1 infected samples.

Culture medium was added to the remaining two wells of each test compound concentration to allow evaluation of cytotoxicity. Each assay plate contained six wells of untreated, uninfected, cell control samples and six wells of untreated, infected, virus control samples 2',3'-Dideoxyinosine (DDI) was assayed in parallel as a positive control compound.

Assay plates were incubated at 37° C. in a humidified, 5% $CO_2$ atmosphere. Twice each day an aliquot of a 100× cysteamine or cystamine concentrate was added to each of the assay wells. The assay plates were observed daily for signs of toxicity and for the appearance of CPE. When the CPE was maximal, samples from each assay well were processed using the colorimetric MTT assay to determine the degree of drug-induced suppression of viral CPE as well as drug cytotoxicity. Quantitation was based on the generation of MTT-formazan by the surviving cells. The results are shown in tabular form below.

TABLE 1

| CYTOTOXICITY EVALUATION | | | |
|---|---|---|---|
| Compound | 1000 μM | 100 μM | 10 μM |
| Cystamine | 5.2 | 96.2 | 108.5 |
| Cysteamine | 3.2 | 120.8 | 101.6 |

| Compound | 100 μM | 32 μM | 10 μM | 3.2 μM | 1.0 μM | 0.32 μM |
|---|---|---|---|---|---|---|
| DDI | 49.0 | 99.0 | 101.2 | 106.3 | 101.0 | 103.4 |

Values shown for cytotoxicity were determined by dividing the absorbance for drug-treated, uninfected samples by the absorbance for cell control samples, then multiplying by 100. The numbers are mean values duplicate wells. Values were calculated relative to the cell control samples for each assay plate.

TABLE 2

| ANTIVIRAL EVALUATION | | | |
|---|---|---|---|
| Compound | 1000 μM | 100 μM | 10 μM |
| Cystamine | TOXIC | 119.3 | 13.1 |
| Cysteamine | TOXIC | 133.0 | 0.0 |

| Compound | 100 μM | 32 μM | 10 μM | 3.2 μM | 1.0 μM | 0.32 μM |
|---|---|---|---|---|---|---|
| DDI | 36.5[a] | 95.2 | 84.4 | 22.8 | 0.0 | 0.0 |

The values shown for antiviral activity are percent inhibition of viral CPE and were calculated using the formula:

$$\frac{\text{Absorbance of drug-tested, infected sample} - \text{Absorbance of virus control}}{(\text{Absorbance cell control}) - (\text{Absorbance virus control})} \times 100$$

The numbers are mean values for duplicate wells. Values were calculated relative to the cell and virus control samples of each assay plate.
[a]Partial drug toxicity at this test concentration may be causing an artificially low value for the antiviral activity As a result of such testing it was found that although cysteamine and cystamine were toxic to the assay cells at a concentration of 1 mM and exhibited little or no antiviral activity at a concentration of 0.01 mM, at a concentration of 0.1 mM cysteamine and cystamine were non-cytotoxic and completely protected the HIV-infected cells from the cytopathic effects of the virus infection.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for treating HIV infection, comprising administering an effective amount of cysteamine, cystamine, phosphocysteamine, or a pharmaceutically acceptable salt thereof to a patient in need thereof.
2. The method of claim 1, further comprising administering an effective amount of AZT or 2', 3'-dideoxyinosine to said patient.
3. A method of treating AIDS, ARC, and lymphadenopathy, comprising administering an effective amount of cysteamine, cystamine, phosphocysteamine, or a pharmaceutically acceptable salt thereof to a patient in need thereof.
4. The method of claim 3, further comprising administering an effective amount of AZT or 3',3'-dideoxyinosine to said patient.
5. The method of claim 1, wherein said cysteamine, cystamine, phosphocysteamine, or a pharmaceutically acceptable salt thereof is administered in the form of a pharmaceutical composition consisting essentially of (i) cysteamine, cystamine, phosphocysteamine, or a pharmaceutically acceptable salt thereof and (ii) a pharmaceutically acceptable carrier.
6. The method of claim 1, wherein said cysteamine, cystamine, phosphocysteamine, or a pharmaceutically acceptable salt thereof is administered in the form of a pharmaceutical composition consisting essentially of (i) cysteamine, cystamine, phosphocysteamine, or a pharmaceutically acceptable salt thereof, (ii) a pharmaceutically acceptable carrier, and (iii) AZT or 2', 3'-dideoxyinosine
7. The method of claim 1, wherein cysteamine is administered.
8. The method of claim 7, wherein said patient is a child and said cysteamine is administered in an amount of 1 to 3 $g/m^2$ of body surface of free base daily in four divided doses.
9. The method of claim 8, wherein said cysteamine is administered in an amount of 1.5 to 2.5 $g/m^2$ of body surface of free base daily in four divided doses.
10. The method of claim 7, wherein said patient is an adult and said cysteamine is administered in an amount of 1 to 3 g of free base q6°.
11. The method of claim 10, wherein said cysteamine is administered in an amount of 1.5 to 2.5 g of free base q6°.
12. The method of claim 3, wherein said cysteamine, cystamine, phosphocysteamine, or a pharmaceutically acceptable salt thereof is administered in the form of a pharmaceutical composition consisting essentially of (i) cysteamine, cystamine, phosphocysteamine, or a pharmaceutically acceptable salt thereof and (ii) a pharmaceutically acceptable carrier.
13. The method of claim 3, wherein said cysteamine, cystamine, phosphocysteamine, or a pharmaceutically acceptable salt thereof is administered in the form of a pharmaceutical composition consisting essentially of (i) cysteamine, cystamine, phosphocysteamine, or a pharmaceutically acceptable salt thereof, (ii) a pharmaceutically acceptable carrier, and (iii) AZT or 2',3'-dideoxyinosine
14. The method of claim 3, wherein cysteamine is administered.
15. The method of claim 14, wherein said patient is a child and said cysteamine is administered in an amount of 1 to 3 $g/m^2$ of body surface of free base daily in four divided doses.
16. The method of claim 15, wherein said cysteamine is administered in an amount of 1.5 to 2.5 $g/m^2$ of body surface of free base daily in four divided doses.
17. The method of claim 14, wherein said patient is an adult and said cysteamine is administered in an amount of 1 to 3 g of free base q6°.
18. The method of claim 17, wherein said cysteamine is administered in an amount of 1.5 to 2.5g of free base q6°.

* * * * *